(12) United States Patent
Daf

(10) Patent No.: US 8,900,534 B2
(45) Date of Patent: Dec. 2, 2014

(54) BIOLOGICAL SAMPLE-PROCESSING APPARATUS HAVING A DOOR WITH SPACE FOR RECEIVING REAGENT TANKS

(75) Inventor: David Daf, Taipei (TW)

(73) Assignee: Taigen Bioscience Corporation, Taipei (TW)

( * ) Notice: Subject to any disclaimer, the term of this patent is extended or adjusted under 35 U.S.C. 154(b) by 85 days.

(21) Appl. No.: 13/560,087

(22) Filed: Jul. 27, 2012

(65) Prior Publication Data

US 2013/0034476 A1   Feb. 7, 2013

(30) Foreign Application Priority Data

Aug. 1, 2011   (TW) .............................. 100127248 A

(51) Int. Cl.
 *B01L 99/00*   (2010.01)
 *G01N 35/10*   (2006.01)
 *G01N 35/00*   (2006.01)
 *B01L 1/00*   (2006.01)

(52) U.S. Cl.
 CPC .. *G01N 35/1002* (2013.01); *G01N 2035/00306* (2013.01); *B01L 1/50* (2013.01)
 USPC .......................................... 422/567; 422/565

(58) Field of Classification Search
 USPC .................. 422/500, 501, 547, 560, 565, 567
 See application file for complete search history.

(56) References Cited

U.S. PATENT DOCUMENTS

| | | | | |
|---|---|---|---|---|
| 6,264,891 | B1 * | 7/2001 | Heyneker et al. | 422/64 |
| 2004/0183417 | A1 * | 9/2004 | Ahmed et al. | 312/408 |
| 2009/0023605 | A1 * | 1/2009 | Lebl et al. | 506/27 |
| 2010/0283366 | A1 * | 11/2010 | Lucas et al. | 312/401 |

* cited by examiner

*Primary Examiner* — Jill Warden
*Assistant Examiner* — Dwayne K Handy
(74) *Attorney, Agent, or Firm* — Hamre, Schumann, Mueller & Larson, P.C.

(57) ABSTRACT

A biological sample-processing apparatus has a sample-processing chamber, which has a door with space for receiving reagent tanks. The reagent supply tanks have conduits in fluid communication with reagent buffer tanks in the sample-processing chamber. The door has a pivot with a hollow interior. At least one conduit connects the reagent supply tanks to the reagent buffer tanks through the hollow interior of the pivot. The present invention provides a modification of the door of a biological sample-processing apparatus so that the door is equipped with reagent supply tanks that contain reagents for processing biological samples and that facilitate the operation of the processing and increase convenience, and further, enable more of the apparatuses to be allocated in the same space.

6 Claims, 4 Drawing Sheets

US 8,900,534 B2

BIOLOGICAL SAMPLE-PROCESSING APPARATUS HAVING A DOOR WITH SPACE FOR RECEIVING REAGENT TANKS

CROSS-REFERENCE TO RELATED APPLICATIONS

This application claims the priority benefit of Taiwan application serial No. 100127248, filed on Aug. 1, 2011, which is incorporated herein by reference.

FIELD OF THE INVENTION

The invention is related to a biological sample-processing apparatus having a door with space for receiving reagent tanks that contain reagents for processing biological samples.

BACKGROUND OF THE INVENTIONS

Reagents are frequently added when a biological apparatus is in operation, as reagents are consumable in sample-processing. This means that they are discarded after sample-processing is completed, and new reagents are added before new sample-processing begins. To enable the process of a biological sample-processing apparatus to be continuous without being interrupted by the addition of reagents, it is necessary for the apparatus to be equipped with reagent supply tanks which are large enough to contain sufficient reagents. The reagent supply tanks are designed to be positioned inside or outside of the sample-processing chamber.

For reagent supply tanks which are positioned inside the sample-processing chamber, such as those shown in FIG. 1, the sample-processing chamber 12 has sufficient space 16 to accommodate at least one such reagent supply tank 14. However, such space 16 would increase the dimensions of a biological sample-processing apparatus in a transverse direction. Reagent supply tanks 14 positioned along the longitudinal direction in the sample-processing chamber 12 would be disadvantageous if manual operation is needed, for example, if an operator needs to use his hand to access deeper parts of the sample-processing chamber 12. Accordingly, the arrangement of reagent supply tanks 14 in a transverse direction would facilitate manual operation. However, arrangement in a transverse direction would also increase the space occupied by the apparatus.

If reagent supply tanks are arranged outside of the sample-processing chamber, the space occupied by the apparatus will not increase. However, for the sake of easy operation, reagent supply tanks should be arranged on the side of the apparatus. However, this would cause the apparatus occupy more space. Although an arrangement in this way would be more convenient for operators compared to an arrangement of the reagent supply tanks in the sample-processing chamber, operation has to be performed at the side of the apparatus. Space needs to be reserved for operation of the apparatus. This causes an uneconomical utilization of space.

In view of the above drawbacks, a way to improve the space efficiency of a biological sample-processing apparatus is desired. The benefits of space efficiency is more apparent when more apparatuses are arranged in juxtaposition. In addition, improvements to the apparatus are also desired for the purpose of allowing easier operation.

SUMMARY OF THE INVENTIONS

The present invention is related to a biological sample-processing apparatus having a door with space for receiving reagent tanks. Apparatus of this kind generally have a sample-processing chamber and a waste liquid storage chamber. The sample-processing chamber is the space wherein sample-processing is performed and the waste liquid storage chamber is the space wherein the waste liquids produced in the processing are temporarily stored before being subsequently removed or discarded at an appropriate time.

The present invention is characterized in that the door of the sample-processing chamber provides space for containing reagents. In practice, reagents are stored in the reagent supply tanks, and the reagent supply tanks are arranged at the inner side of the door of the sample-processing chamber. As such, when addition of the reagent is needed, an operator only needs to open the door of the sample-processing chamber to fill the reagents into the reagent supply tanks, saving him or her the trouble of having to use his or her hand to reach a tank arranged in the sample-processing chamber. Although the thickness of the door should be increased to receive the reagent supply tanks, the thickness is increased inwardly, not outwardly, resulting in an increase in the ease of operation but not the overall volume of the apparatus.

In the present invention, how the reagents are transferred to the sample-processing chamber is a question that is considered. The present invention is further characterized in providing a hollow pivot in the door of the sample-processing chamber. The conduits that connect the reagent supply tanks to the reagent buffer tanks run through the hollow pivot. As such, opening or closing the door of the sample-processing chamber will not hamper the flow of reagents from the reagent supply tanks to the reagent buffer tanks.

While the preferred embodiment has been illustrated and described, it is to be understood that such embodiment should not be interpreted to limit the invention. Numerous modifications, changes, variations, substitutions, and equivalents can be made by those skilled in the art without departing from the spirit and scope of the present invention as defined by the appended claims.

DETAILED DESCRIPTION OF THE PREFERRED EMBODIMENTS

Figure 2:
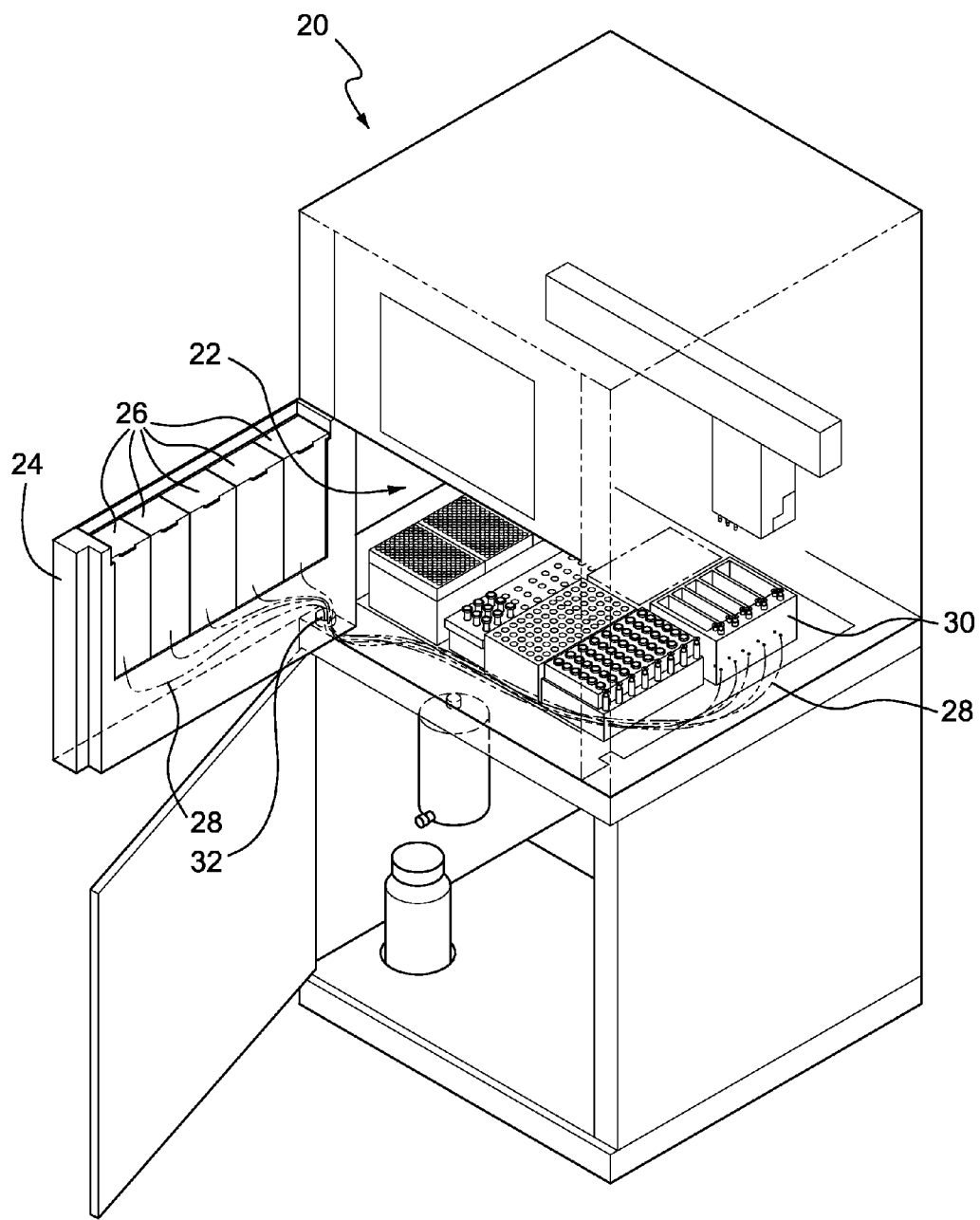
FIG. 2 shows a biological sample-processing apparatus of the present invention, in which the reagent supply tanks are arranged at the inner side of the door of the sample-processing chamber, and the reagent supply tanks are in fluid communication with the reagent buffer tank in the sample-processing chamber through conduits.

The preferred embodiments of the present invention are shown in FIGS. 2-5. FIG. 2 shows a biological sample-processing apparatus 20, which is capable of processing multiple biological samples simultaneously, suitable for laboratories of biomedical research, pharmacodiagnostics, and clinical testing. The biological sample-processing apparatus 20 has a sample-processing chamber 22. The present invention is characterized in that the door of the sample-processing chamber 22 is designed to receive a plurality of reagent supply tanks 26. The reagent supply tanks 26 are used to contain various reagents needed for sample-processing. The number and size of the reagent supply tanks are determined in accordance with practical need. The reagent supply tanks 26 are in fluid communication with the reagent buffer tanks 30. Reagents are transferred from the reagent supply tanks 26 to the reagent buffer tank 30 for processing.

After the operation of sample-processing is completed, the reagents in the reagent buffer tanks 30 should be discarded. The reagents to be discarded are discharged to a waste liquid barrel 38. The operator can, at the appropriate time, discharge the waste liquid to the waste liquid collecting barrel 40, and then remove the waste liquid collecting barrel 40 from the biological sample-processing apparatus 20.

Figure 3:
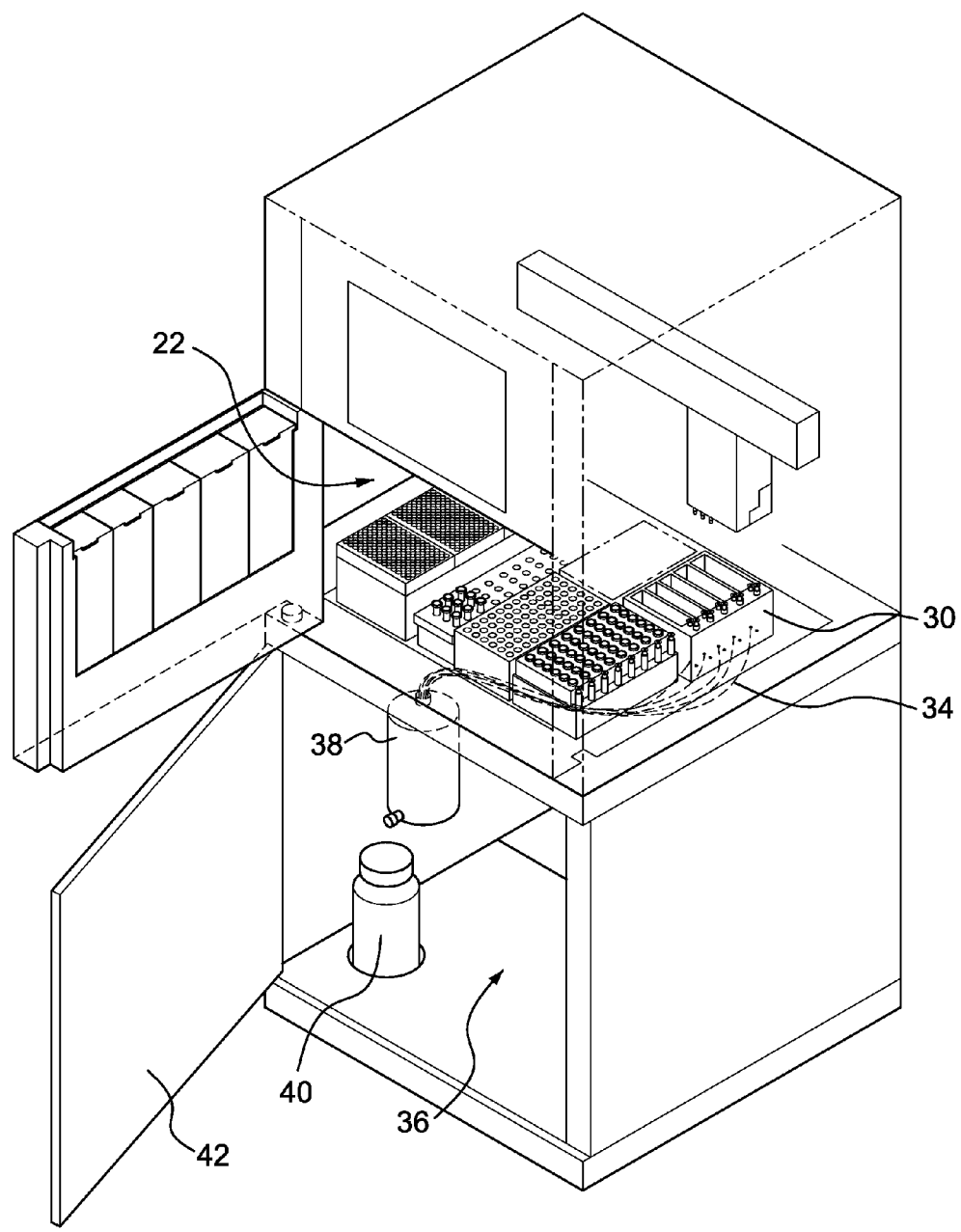
FIG. 3 shows a biological sample-processing apparatus of the present invention, in which the reagent buffer tank is connected to a waste liquid barrel.

As shown in FIG. 3, the waste liquid barrel 38 and the waste liquid collecting barrel 40 are arranged in a waste liquid storage chamber 36. The waste liquid storage chamber 36 is configured to be separate from the sample-processing chamber 22 such that the operator only needs to open the door 42 of the waste liquid storage chamber 36 when the waste liquid collecting barrel 40 is to be removed, and does not interrupt the progress of the sample-processing in the sample-processing chamber 22 in doing so.

Since the reagents are to be discarded once the sample-processing procedures are completed, the reagent buffer tanks 30 will be refilled with new reagents for the subsequent procedures. The reagent supply tanks 26 contain a sufficient supply of reagents for multiple processing procedures in the reagent buffer tanks 30. The reagents, after being supplied from the reagent supply tanks 26 to the reagent buffer tanks 30, are discharged to the waste liquid barrel 38 through programmed automatic control.

Figure 1:
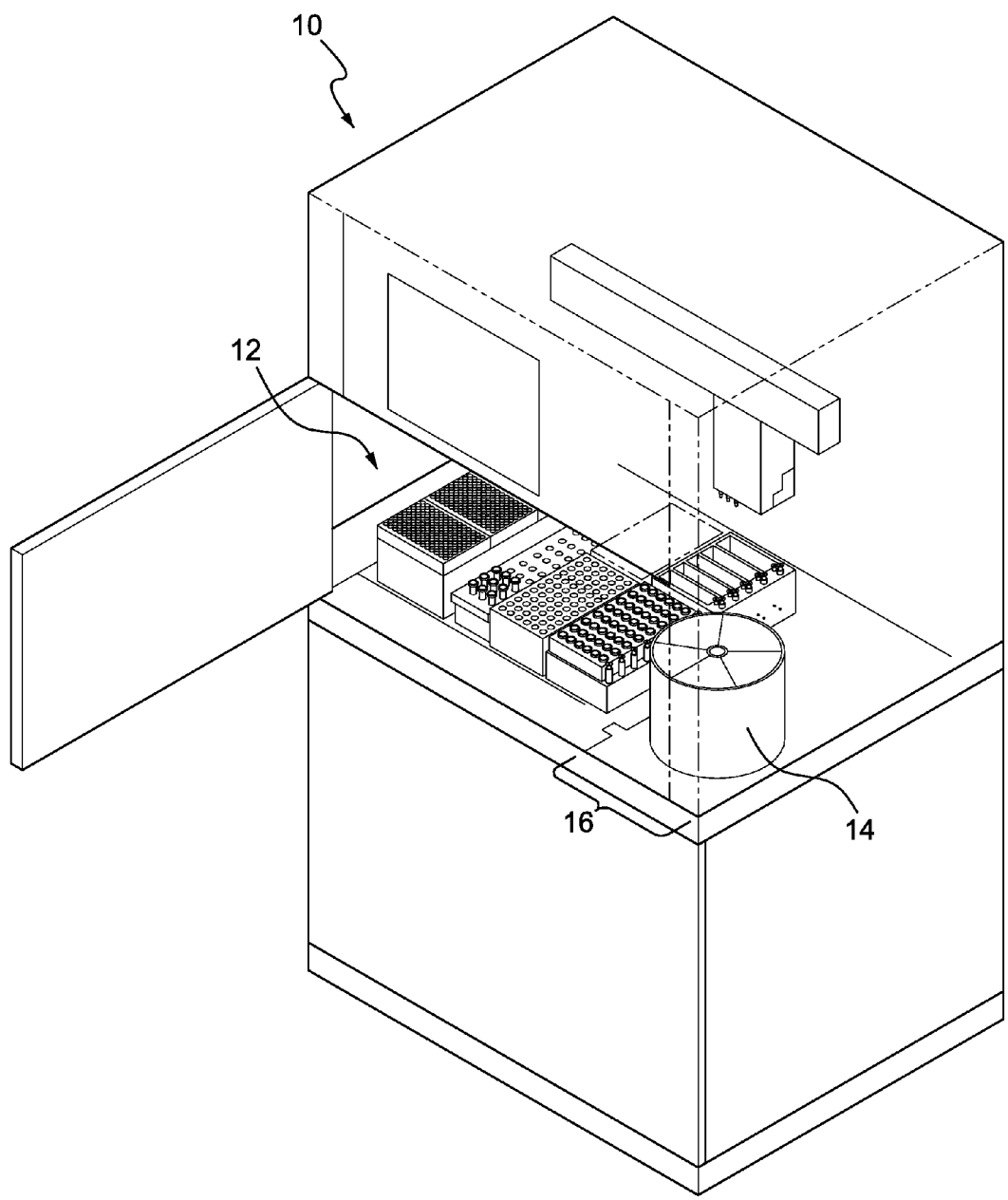
FIG. 1 shows a prior art biological sample-processing apparatus.

Once the reagents in the reagent supply tanks 26 are used up, new reagents will be manually added to the reagent supply tanks 26. As shown in FIG. 2, the reagent supply tanks 26 are arranged at the inner side of the door 24. Referring to FIG. 1, the biological sample-processing apparatus 10 currently used, the reagent supply tanks 14 are arranged in the sample-processing chamber 12. To prevent the apparatus from using too much space, the sample-processing chamber 12 is configured to have limited space. When adding the reagents, operators need to use their hands to access to the interior of the sample-processing chamber 12. However, the limited space of the sample-processing chamber 12 hampers operators' access to the interior of the chamber 12. For the sample-processing chamber 12 of the present invention shown in FIG. 2, when an operator adds reagents, he/she only needs to open the door 24 to access to the reagent supply tanks 26, and their hand does not need to extend to the interior of the sample-processing chamber 22. Thus, if reagent supply tanks 26 are arranged at the inner side of the door 24 of the sample-processing chamber 22, the accessibility of such sample-processing chamber would be enhanced significantly.

Moreover, as shown in FIG. 1, the reagent supply tanks 14 occupy quite a lot of transverse space in the sample-processing chamber 12. The overall biological sample-processing apparatus 10 will inevitably have larger dimensions in width. When multiple biological sample-processing apparatus 10 are juxtaposed, the space will be significantly increased. FIG. 5 shows multiple biological sample-processing apparatuses 20 of the present invention in juxtaposition. In contrast to the prior art apparatus shown in FIG. 1, the arrangement of the reagent supply tanks at the inner side of the door 24 of the sample-processing chamber 22 allows more biological sample-processing apparatus 20 of the present invention to be allocated in the same space.

As shown in FIG. 2, the pivot 32 at the lower corner of the door 24 is made hollow. The conduits 28 that are used to connect the reagent supply tanks 26 and the reagent buffer tanks 30 run in the interior of the door 24 through the hollow pivot 32 and enter the sample-processing chamber 22 of the biological sample-processing apparatus 20. The conduits 28 are arranged in the door 24 and are hidden therein such that they are illustrated in the drawings with broken lines. As the conduits 28 are arranged in the interior of the door 24, they would not hamper the operation of the biological sample-processing apparatus 20 nor affect the aesthetic appearance thereof.

The conduits 28 pass through the hollow pivot 32 and run internally to the reagent buffer tanks 30, and therefore, would not affect the aesthetic appearance of the biological sample-processing apparatus 20.

As shown in FIG. 3, the waste fluid conduits 34 connect the reagent buffer tanks 30 to the waste liquid barrel 38. After the processing procedures are complete, reagents in the reagent buffer tanks 30 flow through the waste fluid conduits 34 to the waste liquid barrel 38 for temporary storage. When the waste fluid (collectively the used reagents) reaches a predetermined level, a valve at the outlet of the waste liquid barrel 38 is opened and the waste fluid is discharged to the waste liquid collecting barrel 40. The waste liquid collecting barrel 40 is removable, and thus the operator can remove it after it is full. In FIG. 3, conduits 28 are omitted and not shown in the figure, and in FIG. 2, the waste fluid conduits 34 are also omitted to avoid adverse effect on clearness of the drawings.

Figure 4:
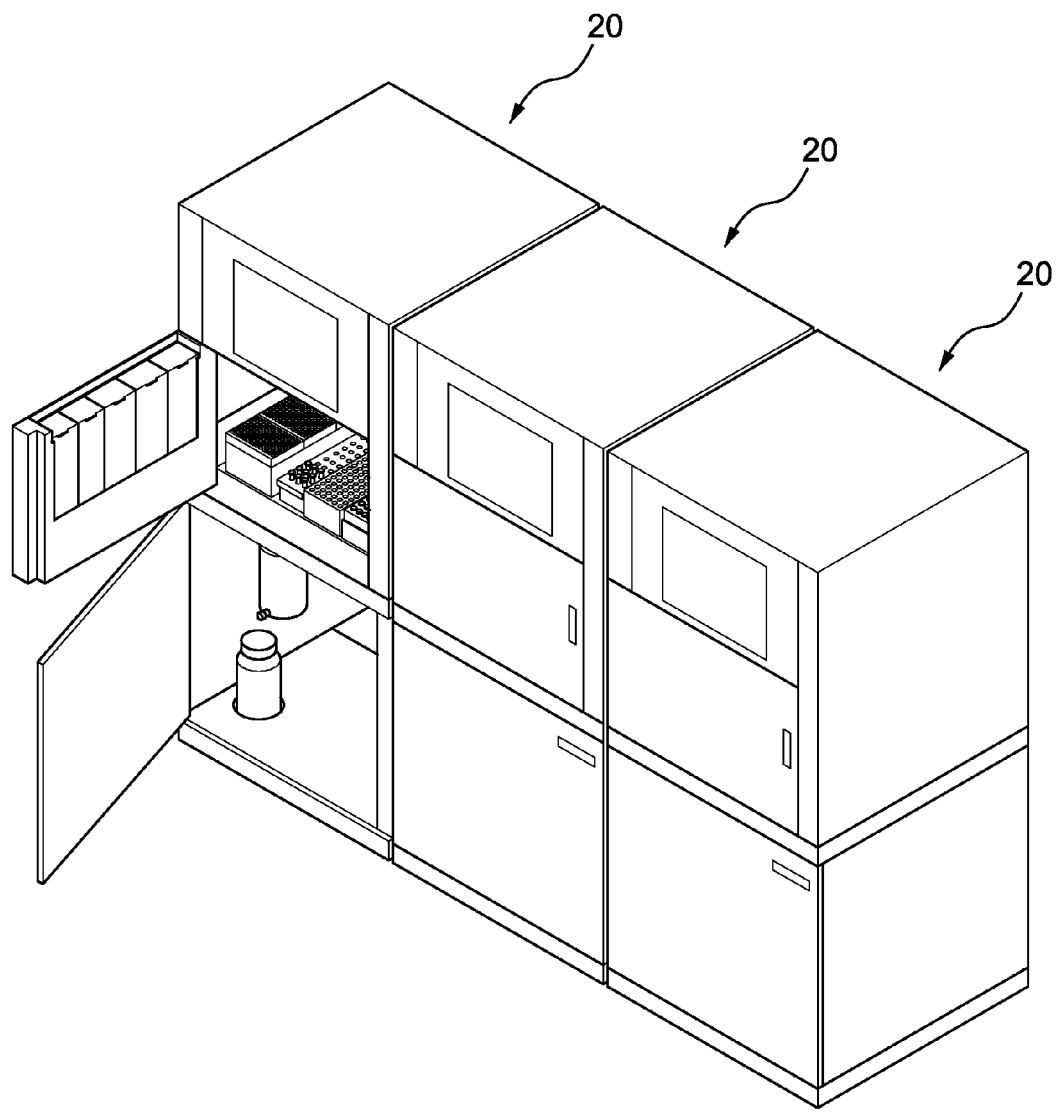
FIG. 4 shows a plurality of biological sample-processing apparatus in juxtaposition.

FIG. 4 shows multiple biological sample-processing apparatus 20 of the present invention in juxtaposition. In the present invention, reagent supply tanks 26 are arranged at the inner side of the door 24. Compared with prior art, in which the reagent supply tanks are arranged in the sample-processing chamber, the present invention can decrease the transverse space of the sample-processing chamber. The decrease in space would allow for the juxtaposition of more biological sample-processing apparatus. When large quantities of samples need to be processed and more biological sample-processing apparatuses are needed, the benefits of this space efficiency would be more prominent.

It can be understood that the biological sample-processing apparatus disclosed in the present invention has the advantage of saving space increased ease of operation, and thus would be highly practical in use.

What is claimed is:

1. A biological sample-processing apparatus having a door with space for receiving reagent tanks, comprising:
    a sample processing chamber having a door with sufficient space that is configured to receive one or more reagent supply tanks;
    one or more reagent supply tanks in the door space;
    one or more reagent buffer tanks disposed inside the chamber, the reagent buffer tanks being connected to the reagent supply tanks through conduits; and
    wherein the door has a hollow pivot at a lower corner thereof, and the conduits connecting the reagent supply tanks and the reagent buffer tanks run through the interior of the door, the pivot, and to the reagent buffer tanks.

2. The biological sample-processing apparatus according to claim 1 further comprising a waste liquid barrel for temporarily storing the reagents of the reagent buffer tanks after processing is completed, and wherein the waste liquid barrel is connected to the reagent buffer tanks through waste fluid conduits.

3. The biological sample-processing apparatus according to claim 2 further comprising a waste liquid collecting barrel to collect the reagents temporarily stored in the waste liquid barrel.

4. The biological sample-processing apparatus according to claim 3 further comprising a waste liquid storage chamber for receiving a waste liquid barrel and a waste liquid collecting barrel, and the waste liquid storage chamber is separated from the sample-processing chamber.

5. The biological sample-processing apparatus according to claim 1, wherein the door is a side door and the door is configured to rotate around a vertical axis via the pivot.

6. The biological sample-processing apparatus according to claim 1, wherein the pivot extends vertically from a first end to a second end, and the conduits pass through the pivot from the first end to the second end.

\* \* \* \* \*